(12) United States Patent
Zehavi et al.

(10) Patent No.: US 10,777,315 B2
(45) Date of Patent: Sep. 15, 2020

(54) GLOBAL SPINAL ALIGNMENT METHOD

(71) Applicant: MAZOR ROBOTICS LTD., Caesarea (IL)

(72) Inventors: Eliyahu Zehavi, Haifa (IL); Yossi Bar, Haifa (IL); Shlomit Steinberg, Tel Aviv (IL); Leonid Kleyman, Misgav (IL); Isador Lieberman, Plano, TX (US)

(73) Assignee: MAZOR ROBOTICS LTD., Caesarea (IL)

( * ) Notice: Subject to any disclaimer, the term of this patent is extended or adjusted under 35 U.S.C. 154(b) by 40 days.

(21) Appl. No.: 15/765,720

(22) PCT Filed: Oct. 13, 2016

(86) PCT No.: PCT/IL2016/051121
§ 371 (c)(1),
(2) Date: Apr. 4, 2018

(87) PCT Pub. No.: WO2017/064719
PCT Pub. Date: Apr. 20, 2017

(65) Prior Publication Data
US 2018/0301213 A1  Oct. 18, 2018

Related U.S. Application Data

(60) Provisional application No. 62/240,751, filed on Oct. 13, 2015.

(51) Int. Cl.
*G16H 20/40* (2018.01)
*G16H 30/40* (2018.01)
(Continued)

(52) U.S. Cl.
CPC ............ *G16H 20/40* (2018.01); *A61B 6/032* (2013.01); *A61B 6/505* (2013.01); *A61B 6/5217* (2013.01);
(Continued)

(58) Field of Classification Search
None
See application file for complete search history.

(56) References Cited

U.S. PATENT DOCUMENTS 5,706,324 A  1/1998  Wiesent et al.
6,038,282 A  3/2000  Wiesent et al.
(Continued)

OTHER PUBLICATIONS

Majdouline, Younes, et al. "Computer simulation for the optimization of instrumentation strategies in adolescent idiopathic scoliosis." Medical & biological engineering & computing 47.11 (2009): 1143. (Year: 2009).*

(Continued)

*Primary Examiner* — David F Dunphy
(74) *Attorney, Agent, or Firm* — Sheridan Ross P.C.

(57) ABSTRACT

A method of planning the correction of spinal deformations of a subject, by performing segmentation on a three dimensional image of the subject's spine in its erect neutral position, such that the positions and orientations of the vertebrae in a region of interest are characterized. Parameters relating to the alignment and position of the vertebrae are derived from the segmentation, followed by determining whether the parameters fall within an acceptable range desired for the spine of the subject. If not within the acceptable range, an alignment optimization is performed on the vertebrae to bring the parameters within the acceptable range, to reduce the spinal deformations of the subject's spine. The alignment optimization is performed by taking into consideration limitations arising from the dynamic range of motion of the vertebrae as determined by analyzing images of the subject's spine, while the subject is in positions of maximum bending.

21 Claims, 6 Drawing Sheets

(51) Int. Cl.
| | |
|---|---|
| A61B 34/10 | (2016.01) |
| A61B 6/03 | (2006.01) |
| A61B 6/00 | (2006.01) |
| G06T 7/00 | (2017.01) |
| G06T 7/73 | (2017.01) |
| G06T 7/11 | (2017.01) |
| G06T 7/70 | (2017.01) |
| G16H 50/50 | (2018.01) |
| G16H 50/20 | (2018.01) |

(52) U.S. Cl.
CPC ............ *A61B 6/5235* (2013.01); *A61B 34/10* (2016.02); *G06T 7/0012* (2013.01); *G06T 7/11* (2017.01); *G06T 7/70* (2017.01); *G06T 7/73* (2017.01); *G16H 30/40* (2018.01); *G16H 50/50* (2018.01); *A61B 2034/104* (2016.02); *A61B 2034/105* (2016.02); *G06T 2207/10081* (2013.01); *G06T 2207/30012* (2013.01); *G16H 50/20* (2018.01)

(56) References Cited

U.S. PATENT DOCUMENTS

| | | | |
|---|---|---|---|
| 6,049,582 | A | 4/2000 | Navab |
| 6,226,548 | B1 | 5/2001 | Foley et al. |
| 6,322,567 | B1 | 11/2001 | Mittelstadt et al. |
| 7,142,633 | B2 | 11/2006 | Eberhard et al. |
| 7,542,791 | B2 | 6/2009 | Mire et al. |
| 8,705,817 | B2 | 4/2014 | Saint Felix et al. |
| 9,119,555 | B2 | 9/2015 | Le Bras |
| 2005/0119593 | A1* | 6/2005 | Gallard .............. A61B 17/7074 600/594 |
| 2006/0182216 | A1 | 8/2006 | Lauritsch et al. |
| 2006/0204069 | A1 | 9/2006 | Le Bras |
| 2007/0249911 | A1 | 10/2007 | Simon et al. |
| 2013/0020179 | A1 | 8/2013 | Illes et al. |
| 2013/0307955 | A1 | 11/2013 | Deitz et al. |
| 2014/0018711 | A1* | 1/2014 | Philipson .................. A61H 1/00 601/38 |
| 2015/0190187 | A1 | 7/2015 | Parent et al. |
| 2015/0282796 | A1 | 10/2015 | Nawana et al. |
| 2016/0242857 | A1* | 8/2016 | Scholl ................ A61B 17/8863 |
| 2017/0135770 | A1* | 5/2017 | Scholl .................... A61B 34/10 |
| 2017/0143426 | A1* | 5/2017 | Isaacs ..................... G16H 50/50 |
| 2017/0231709 | A1* | 8/2017 | Gupta ..................... A61B 34/20 600/424 |
| 2018/0098715 | A1* | 4/2018 | Deitz ..................... A61B 34/10 |
| 2018/0271602 | A1* | 9/2018 | Frey ....................... A61B 34/10 |
| 2019/0099221 | A1* | 4/2019 | Schmidt ................. G16H 50/50 |

OTHER PUBLICATIONS

Wang, Xiaoyu, et al. "Biomechanical modeling and analysis of a direct incremental segmental translation system for the instrumentation of scoliotic deformities." Clinical Biomechanics26.6 (2011): 548-555. (Year: 2011).*

Klepps et al, "Prospective Comparison of Flexibility Radiographs in Adolescent Idiopathic Scoliosis", 2001, SPINE vol. 26, No. 5, pp. E74-E79 (Year: 2001).*

International Search Report and Written Opinion of PCT/IL2016/051121 dated Feb. 9, 2017.

"Adult Spinal Deformity: Sagittal Imbalance" by J.M. Cavanilles-Walker et al, published in International Journal of Orthopedics, vol. 1(3) pp. 64-72 (2014).

Correlation of Pelvic and Spinal Parameters in Adult Deformity Patients with Neutral Sagittal Imbalance by D. Deinlein et al, published in Spine Deformity, vol. 1, pp. 458-463 (2013).

"Use of Surgimap Spine in Sagittal Plane Analysis, Osteotomy Planning and Correction Calculation" by M. Akbar et al, published in Neurosurg. Clin. N. Am., vol. 24, pp. 163-172 (2013).

"Spino-Pelvic Parameters after Surgery can be Predicted" by V. Lafage et al, published in SPINE, vol. 36, No. 13, pp. 1037-1045 (2011).

"Standing Balance and Sagittal Plane Spinal Deformity: Analysis of Spinopelvic and Gravity Line Parameters" by Lafage et al, published in Spine vol. 33(14) pp. 1572-1578 (2008).

"The radiographic method for evaluation of axial vertebral rotation" by Cerny et al, published in Scoliosis vol. 9(11) (2014).

European Supplemental Search Report and Written Opinion of EP application 16 85 5071 dated Jul. 18, 2019.

Younes M et al. "Computer simulation for the optimization of instrumentation strategies in adolescent idiopathic scoliosis," Medical and Biological Engineering and Computing; Springer, Berlin vol. 47, No. 11, Aug. 11, 2009, pp. 1143-1154.

Aubin CE et al. "Preoperative planning simulator for spinal deformity surgeries," Spine: an international journal for the study of the spine, vol. 33, No. 20, Sep. 1, 2008, pp. 2143-2152.

Wang X et al. "Biomechanical modeling and analysis of a direct incremental segmental translation system for the instrumentation of scoliotic deformities," Clinical Biomechanics, vol. 26, No. 6, Jul. 1, 2011, pp. 548-555.

Aurouer N et al., "Computerized preoperative planning for correction of sagittal deformity of the spine," Surgical and Radiologic Anatomy, Springer-Verlag, PA, vol. 31, No. 10, Jul. 14, 2009, pp. 781-792.

Li G, et al, "Segmental in vivo vertebral motion during functional human lumbar spine activities," European Spine Journal, Springer, Berlin, vol. 18, No. 7, Mar. 20, 2009, pp. 1013-1021.

European Board of Appeals, Decision of Jul. 12, 2005 in case No. T 0914/02-3.4.1; application No. 97300544.0.

European Board of Appeals, Datasheet for the interlocutory decision of Feb. 22, 2019 in case No. T 0489/14-3.5.07; application No. 03793825.5.

* cited by examiner

FIG. 4A  Axial

FIG. 4B  Lateral

GLOBAL SPINAL ALIGNMENT METHOD

FIELD OF THE INVENTION

The present invention relates to the field of surgical planning for the correction of spinal deformities, especially by using the measured spinal mobility limitations over substantial lengths of the patient's spine in order to plan a correction procedure with minimal surgical corrective steps.

BACKGROUND

The importance of sagittal plane analysis and global sagittal balance and the parameters associated therewith has been widely studied of late, such as in the articles entitled "Adult Spinal Deformity: Sagittal Imbalance" by J. M. Cavanilles-Walker et al, published in International Journal of Orthopedics, Vol. 1(3) pages 64-72 (2014), and "Correlation of Pelvic and Spinal Parameters in Adult Deformity Patients with Neutral Sagittal Imbalance" by D. Deinlein et al, published in Spine Deformity, vol. 1, pages 458-463 (2013), and "Use of Surgimap Spine In Sagittal Plane Analysis, Osteotomy Planning and Correction Calculation" by M. Akbar et al, published in Neurosurg. Clin. N. Am., Vol. 24, pages 163-172 (2013), and "Spino-Pelvic Parameters after Surgery can be Predicted" by V. Lafage et al, published in SPINE, Vol. 36, No. 13, pp. 1037-1045 (2011).

One of the primary objects in correction of spinal deformities is to enable the patient to maintain a natural balance without incurring any stress or pain to maintain that balance. In a normal person, the balance is determined by the various angles of the curvatures of the spine, and specific distances between certain spinal anatomies. These angles and distances, and especially the lumbar lordosis and the thoracic kyphosis in the Sagittal plane and certain pelvic parameters, and the Cobb angle in the Coronal plane and the apical vertebral translation have certain accepted "normal" values, including standard deviation margins, such that when a person with a normally curved spine stands straight, in a posture in which he has no or minimized back pain, these angles and linear distances are within the limits defined as normal As stated in the above referenced Cavanilles article, and others, a main purpose of the pelvic, lordotic and kyphotic spine segments is to balance the head over the pelvis in an energy-efficient position, allowing the C7 plumb line, a vertical line drawn from the center of the C7 vertebral body, to pass as close as possible to the posterior-superior corner of S1. This line is known as the sagittal vertical axis (SVA), and although it is only one alternative parameter used to determine correct spinal posture, it is currently one of the most commonly used radiographic parameters in the evaluation of sagittal plane deformities. Another such parameter in common use includes the T1 Spino-Pelvic Inclination (T1SP1). Additionally, a number of coronal measurements are also used.

Figure 1:
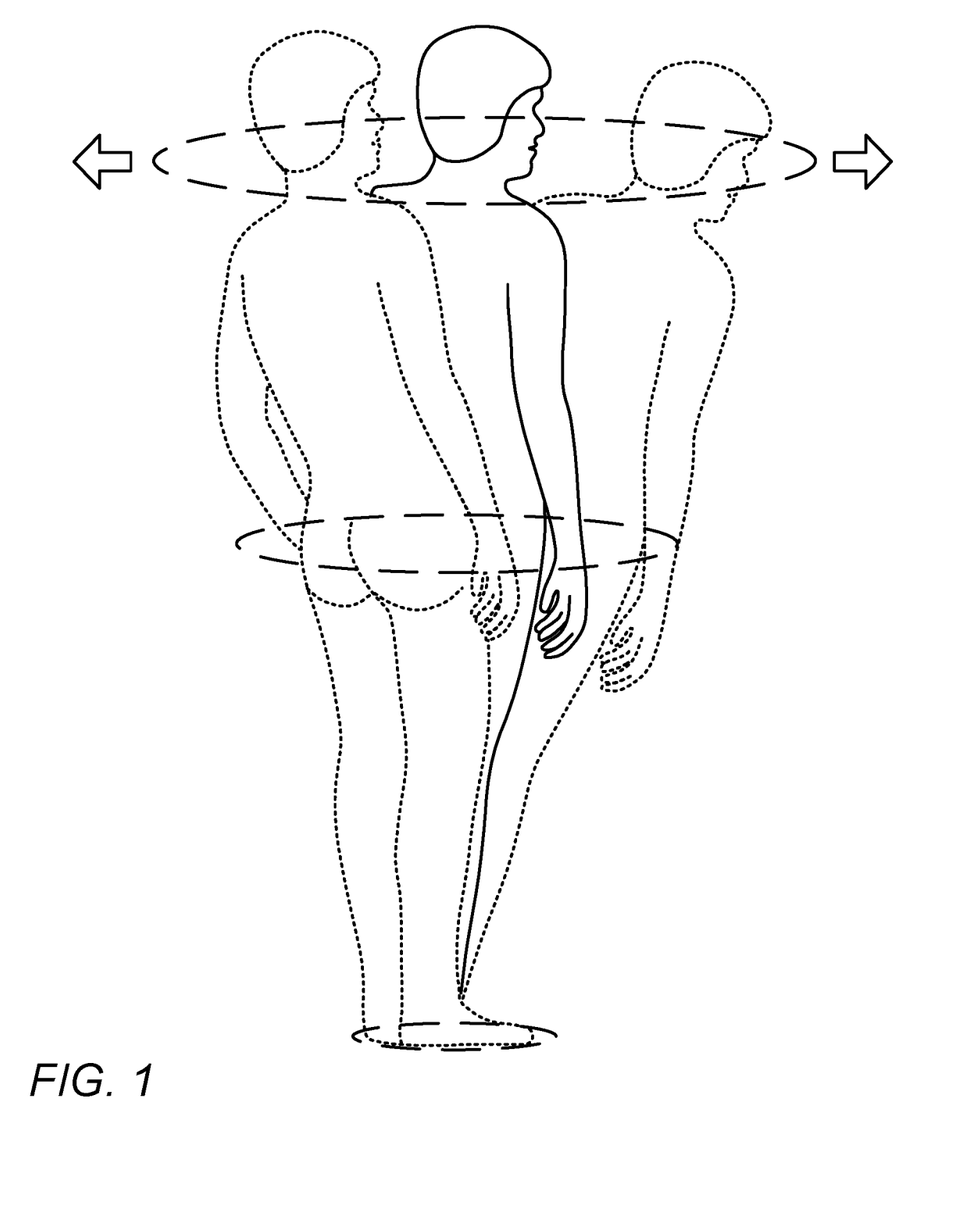
FIG. 1 shows schematically a cone representing the spatial extent of a sense of correct balance by the subject.

Reference is now made to FIG. 1, as taught by J. Dubousset in the article "Three-dimensional analysis of the scoliotic deformity" published in the book "The Pediatric Spine: Principles and Practice" Raven Press, NY, pp. 479-496 (1994). FIG. 1 illustrates schematically what is known as the "Cone of Economy", which is the spatial volume in which the subject feels that his/her body remains in an ergonomically favorable position of balance, with the optimum position being, of course, in the center of the cone. Deviations outside of this cone require external support for the subject to feel in balance. Any sufficiently serious spinal deformity can cause the subject's posture to fall outside of this cone, and there are a number of spinal parameters used to characterize when this situation occurs, as outlined hereinbelow.

In a subject having a healthy spinal deportment, the SVA should fall no further than a few millimeters from the posterior-superior corner of S1. If the subject has spinal deformities which cause a larger divergence of the SVA, the person may have the feeling that he is not in balance, and the brain constantly directs the person to strain his posture in order to attempt to correct his balance, this generally resulting in back pain, and is not always effective in restoring balance or stability of the patient. In order to maintain some sort of sagittal balance, the patient may use different compensatory mechanisms, such as pelvic retroversion, hip extension or knee flexion. The main objective of these mechanisms is to allow the patient to keep an erect position in an energy-efficient way. Maintaining these positions against the clinical status of the patient's spine generates fatigue and muscular or skeletal back pain, which may or may not require surgical correction, but once the spinal deformity is sufficiently large to surpass these compensatory mechanisms, surgical intervention is generally required.

Such surgical correction is designed to achieve restoration of sagittal plane alignment, and can include both fusion and osteotomy procedures, and soft tissue (ligament) release. Spinal osteotomies are often used as part of a spinal reconstructive procedure to achieve spinal balance, stability and correct spinal alignment. A wedge of bone is resected from part of one or more vertebral segments to realign the spine to a better curvature to provide better sagittal balance. Several different osteotomy procedures have been developed, including the Smith-Peterson osteotomy, pedicle subtraction osteotomy, and vertebral column resection, some of which have been in use for many decades. However, if the correction is not done accurately, the person may still have a feeling of imbalance and/or pain, and may continue to try and "straighten" his back, or correct his posture, without generally succeeding in overcoming his problem. As will be discussed hereinbelow, this situation may result either from the non-iterative nature of the programs used to plan spinal curvature correction, or from the often intuitive nature of the decisions made by the surgeon. Examples of these situations can be found in the article entitled "Long-term investigation of nonsurgical treatment for thoracolumbar and lumbar burst fractures: an outcome analysis in sight of spinopelvic balance" by H. Koller et al., published in Eur. Spine J. Vol. 17(8), pp. 1073-1095 (August 2008).

A number of software programs are available commercially, designed for assisting the doctor in planning the optimum surgical procedures in order to correct such spinal deformities. Most of these programs operate on 2-dimensional X-ray images, though some offer planning routines based on 3-D CT or MRI images data sets.

A large number of parameters for defining spinal geometry have been proposed. One currently available software suite, has over 20 parameters which the doctor can manipulate in planning a procedure to restore correct posture to the patient's spine. The software has the ability to calculate "over twenty measurements in a few simple clicks", in order to plan correct sagittal alignment. The doctor uses the 2-D sagittal image of the spine and makes virtual adjustments of the vertebral positions on the image, generating greater or lesser curvatures in the image of spine, in order to obtain the estimated optimum curvature.

However, because of the complexity of the planning procedure, in practice, what is often done is that the surgeon makes the sectioning according to his best judgement and intuition when looking at the images. This arises because of the complexity and multiplicity of parameters which the doctor has to manipulate in order to select the correct resection procedure, as illustrated above. Additionally, the planning is performed on a preliminarily obtained static image (or set of images in the case of a 3-D imaging process), taken of the patient standing, but corrected for the different form of the spine between the supine and standing positions of the patient. In the case of an image obtained from a CT data set of the patient in a prone position, similar to that during surgery, such a correction is not necessary.

Some prior art software programs for predicting graphically a plan for corrective surgical intervention, suggest 2-dimensional correction and therefore don't demonstrate how the coronal correction, for instance, will affect the axial and sagittal planes and vice versa. Furthermore, the surgeon often plans corrections to the patient's spinal curvature on a local basis, regarding just a pair or few vertebrae for each correction step, and generally based on the surgeon's experience, knowledge and intuitiveness, rather than on measured parameters. There is therefore a need to augment this largely qualitative correction approach using quantitative data. Limitations of presently used methods may play a part in the recently estimated statistic that up to one third of kyphosis surgeries in adults are revisions of previously attempted corrections, and that up to 7% of scoliotic corrections in pediatric cases require revisions.

One of the problems of possible software programs for planning spinal correction surgery may be that they could be considered as operating in a manner similar to graphic engineering design programs. The patient's spine could be adjusted in the same way as an engineer may, for instance, design a product using a CAD program. In a graphical plan, anything is allowable to achieve the desired shape. However the patient's spinal structure has preexisting limitations by the clinical situation of each vertebra and vertebra. Therefore, although correction of a defective spinal curvature by osteotomy and fusion procedures may appear possible on a virtual planning program, the clinical limitations of the patient's back may not enable this procedure to be successfully accomplished. And even if such a correction is achieved, it may be at the expense of performing surgical procedures on more vertebra than may be required by a surgically more economic overall method, such as that to be described in the present disclosure.

There therefore exists a need for a system and method which can generate a surgical plan for spinal curvature correction, preferably taking into account the individual capabilities of the patient's motion range, and which provides a more accurate clinical correction plan for the patient's deformities.

The disclosures of each of the publications mentioned in this section and in other sections of the specification, are hereby incorporated by reference, each in its entirety.

SUMMARY

The described methods of this disclosure enable the planning of a spinal surgical correction procedure by pre-analyzing the rigidity and mobility of segments or even of the individual vertebrae in the spine, and hence assisting the surgeon in pre planning the surgical procedures used. This can potentially reduce the level of surgical procedures such as osteotomies or posterior release to be performed in the correction.

In order to overcome the limitations of prior art surgical planning programs that do not take into account the rigidity and mobility of the vertebrae of the particular patient's spine, the currently proposed method and system utilizes a number of preoperative images, most conveniently two dimensional X-ray images, in order to determine the limits of motion or dynamic range of motion of essentially all of the patient's vertebrae, including those which may not ultimately need to be subject to operative procedures. These imaged limits may then be used in order to limit the correction procedure to be planned, so that it will take into account more accurately the patient's personal clinical situation. In order to accomplish this aim, a number of additional X-ray images are taken with the patient's spine in different predefined positions. Thus, images are taken while the patient is told to bend his spine as far as is comfortably possible, in order to determine the natural limit of motion of the spine for that particular patient. In this disclosure, such bending may be alternatively termed, and also thuswise claimed, as "maximum bending", "full bending", "the limit of achievable bending", or similar terms, and it is to be understood that these terms represent similar actions, and are not intended to represent greater or lesser levels of bending. Typically, such bending images are generated in four different directions—with the patient bending to the left and to the right, and with the patient in flexion and in extension. In addition X-ray images of the patient standing straight are also acquired, both AP and lateral, thus providing a total of up to six separate images showing the limitations of motion of the patient's spine at every vertebra. Images of the spine twisted in both directions may also optionally be used to provide additional data, and any other patient positions which may provide useful data for the determination of spinal mobility may also be used.

The information obtained from these preparatory 2-D images thus defines the bio-mechanical properties of each vertebra pair, characterizing the rigidity and the limit of motion of each vertebra relative to its immediate neighbors. In effect, the preliminary 2-D images enable a complete study of the spinal stiffness of the patient to be performed, showing the weak and strong points of the spine's mobility, and enabling the surgery to be concentrated at the stiffer regions of the patient's spine. The surgeon can also plan which spinal anatomy features needs to be 'released' by resection and which anatomy does not need to be resected, this information being important since by avoiding the need for surgical correction, the ligament structure in that region is conserved, which is an important factor for maintaining spinal stability.

The images of the vertebrae, with their local motion limits, can be implanted into a 3-D image set of the spine, based on CT image data of the spine. Use of a real CT image of the particular patient's spine, rather than a standard model of the spine, as typically used in some prior art methods, presents a true clinical picture of the limits of motion of the spine, based on the patient's actual intervertebral motion abilities, impressed upon the patient's actual CT spinal image, including all of the anomalies and defects of that patient's spine. The advantage of such an arrangement is that the optimum surgical correction can then be planned on the global motion of the entire spine, so that no vertebra is stretched beyond the limit which the patient's anatomy allows, unless such a limit would prevent the desired overall curvature from being achieved. This global view of the spine thus also enables the desired spinal shape to be obtained with less surgical intervention than in prior art arrangements, since the spinal shape plan can determine iteratively, which of the patient's vertebrae are better candidates than others for surgery to assist in achieving the desired overall shape. Accordingly, the presently described method should recommend that release procedures be performed preferentially on those vertebrae which have the most rigid bio-mechanical properties, since that is where the optimum benefit will be obtained in the overall correction procedure.

In some of the prior art arrangements, the surgeon simply corrects the spinal curvature based on the deviation of the 2-D images from the ideal, using some of the parameters to define the ideal spinal curvature. The virtual spine image is "moved" on the display to provide the desired curvatures and shape so that the selected spinal parameters achieve the desired values, characteristic of normalized spinal deportment. Once this shape has been finalized, the surgeon then inspects the resultant desired spinal shape, including measurement of the angles and parameters resulting from the new spinal shape, and establishes which vertebrae need surgical modification in order to meet the desired shape and curvatures. Such modification could be freeing intervertebral motion by facet release procedures, osteotomy procedures to change the vertebral orientation sufficiently, and fusion between adjacent vertebrae to provide additional support. However, such a correction based on making local compensations to achieve an overall corrected image may not be the optimum solution, since it may attempt to compensate the curvature at disadvantageous regions. Such a non-optimal solution could arise, for instance if surgical correction is proposed on vertebrae at suggested locations, when those vertebrae do in fact have the bio-mechanical mobility required to provide the optimal overall spinal form, without undergoing any surgical procedures. A less drastic surgical procedure could thus be proposed, if adjustments were made elsewhere to other vertebrae on the spine, enabling those first vertebrae to use their inherent bio-mechanical mobility. At the same time, such prior art solutions may ignore regions where compensation would be much more effective in achieving overall sagittal balance because the apparent purely local need to adjust those vertebrae, as determined from the monitor-adjusted image of the spine, may be low. These techniques may entail cutting away of parts of specific vertebra to enable local motion of the spine in those regions where motion is limited. This is a localized solution, and because of that, it may entail more drastic surgical resection than is necessary.

The techniques described in the present disclosure, in which a global view of the spine is used, make it possible to achieve the desired motion by correction also in vertebrae remote from the problematic region, and thus to use less drastic surgery on the vertebrae identified in prior procedures as being the major cause of the patient's problem.

In contrast to the prior art methods, one of the methods described in the present disclosure can utilize an automatic registration method that generates a proposed spinal reconstruction, which utilizes the envelope of maximum motion which each vertebra and vertebra of the entire spine is capable of performing. A mathematical model can then be determined which takes into account the limitation of the mobility of each individual vertebra, including for instance, the permitted mutual motion of adjacent vertebrae. The latter is important for patients who may have partially fused adjacent vertebrae, whether naturally or by a previous operative procedure. In such cases, when the patient bends, some adjacent fused vertebrae will not move relative to each other. The planning program of the present disclosure takes into account these clinical limitations and will not allow any planned curvature model in which a local motion contravenes the predetermined limitations of the patient's vertebrae in that region of the spine. This affects the potential of correction during surgery—the spine won't align to the planned fusion rod if the deformity is structural, other than by releasing the spinal anatomy in that region surgically. At locations where the planned curvature would result in motion in excess of the patient's spinal mobility at that location, the program will indicate that an osteotomic resection of the vertebral body, or a release procedure for removal of the facet joint or pedicle constraints is required at that vertebral level, in order to enable the desired angle or position correction to be achieved. Thus the spinal corrections proposed are limited by the clinical abilities of the patient. Such limitations are not generally taken into account in the prior art planning systems. In the present proposed system, the CT mathematical model on which the planning is performed is brought into line with the actual clinical status of the patient. Thus the patient's spine may be considered to have been converted into the mathematical model on which the planning is performed. Therefore, any proposed curvature corrections performed graphically on the software model are close to the curvature corrections performed on the spine of the client itself. In that respect, the measurement capabilities available to the surgeon from the software display are restrained, if not completely automatically determined, by the actual clinical status of the patient's spine, and assist in providing the surgeon with the data needed in order to make the correct planning decisions based on the patient's actual situation. This may result in less drastic surgery being undertaken than with prior art programs, since the natural limitations of the patient are taken into account, as well as the compensatory mechanisms that are implemented in the mathematical method that suggests the optimal alignment. This is in contrast to prior art situations in which a model of the spine is adjusted to an optimum curvature without taking into account such individual anatomical/biomechanical constraints as determined by the patient's individual clinical data. While prior art programs may be based on automatic measurements on the spinal model, the presently proposed system may be considered to relate to automatic correction instructions. These automatic correction instructions may include not only surgical instructions as to where and what surgical correction is required, but the program can also, for instance, output the correctly shaped rod to be used at each level where fusion is suggested, in accordance with the correction proposed, and can also propose the screw positions and orientations for fixing those rods. The procedure can also instruct a rod bending apparatus which will enable the correctly shaped rod to be prepared on site in accordance with the correction proposed, as described in co-pending PCT Application published as International Patent Application No. WO 2016/088130 for "Shaper for Vertebral Fixation Rods" having common applicant with the present application.

The present methods thus provide a procedure for calculating the optimal predicted global alignment suggestion of the spine automatically in three dimensions, by analyzing the pre and post planned spinal data, while also taking into account the effect of the subject's clinical mobility at the vertebral level.

The result of performing the methods of this disclosure enables a more global correction of the subject's spinal alignment to be obtained, extending beyond the region of interest of the spine which the surgeon is dealing with. Such a global approach results in what could be termed a head-to-toe alignment, since the subject can thereby achieve a situation in which the spring correction enables universal balance to be achieved, for instance, with the head centered over the pelvis at the spinal midline, and not protruding significantly from the patient's line of center of gravity.

Thus, the alignment assessment or optimization is performed by measuring the full-body projected posture of the subject or sub-elements of the body, for example by assessing the head position as being centered to the midline, above the body's center of gravity, with the forward gaze parallel to the ground.

Alternatively, the amount of flexion in the lower extremity joints during neutral standing can be minimized. The subject's posture and stability can thus be improved by use of these procedures.

Though the above summary of the methods of the present invention have been largely described in terms of the correction of lack of sagittal balance, it is to be understood that the method also involves correction of scoliosis related problems, and the use of a three-dimensional analytic model enables both of these problems to be tackled simultaneously and iteratively.

There is thus provided in accordance with an exemplary implementation of the methods described in this disclosure, a method of planning the correction of spinal deformations of a subject, comprising:
(i) deriving three-dimensional images of the subject's spine in its erect neutral position,
(ii) performing segmentation of at least one three dimensional image such that the positions and orientations of vertebrae in a region of interest of the spine are characterized,
(iii) determining the dynamic range of motion of the vertebrae by analyzing images of the subject's spine in positions of bending of the subject,
(iv) deriving parameters from the segmentation that relate to the alignment and position of the vertebrae in the region of interest,
(v) determining if the parameters fall within an acceptable range of parameters desired for the spine of the subject, and
(vi) performing alignment optimization of at least the vertebrae in the region of interest of the spine to bring the parameters within the acceptable range, to reduce the spinal deformations of the subject's spine,
wherein the alignment optimization is performed by taking into consideration at least limitations arising from the dynamic range of motion of the vertebrae.

In such a method, the alignment optimization may be performed by also taking into consideration biomechanical considerations over the entire length of the subject's spine. In either of these cases, the parameters may relate to at least some of the mutual angles, projections and linear positions which the vertebrae in the region of interest generate along the subject's spine. Additionally, the determining as to whether the parameters may fall within an acceptable range of parameters is performed either automatically by image processing, or by manual measurement on images, or by the judgement or experience of medical personnel.

According to a further implementation of the above methods of the present disclosure, taking into consideration of at least limitations arising from the dynamic range of motion of the vertebrae may comprise the limiting of the motion of the vertebrae to an amended optimized position by a level not exceeding the dynamic range of motion. Alternatively, the taking into consideration of limitations arising from the dynamic range of motion of the vertebrae may comprise an unlimited alignment optimization of the vertebrae of the spine, followed by surgical intervention on at least some of the vertebrae whose dynamic range of motion is less than the motion mandated by execution of the unlimited alignment optimization of the vertebrae of the spine.

In any of the above described methods, the positions of bending of the subject may comprise at least one of bending to the right, bending to the left, bending in flexion, bending in extension, and rotation. Furthermore, the alignment optimization to reduce spinal deformations may comprise an optimization to generate a straightened spinal alignment in the coronal plane, or an optimization of the spinal alignment in the sagittal plane. In the latter case, the optimization of the spinal alignment in the sagittal plane may involve manipulation of sagittal parameters according to a procedure which generates a sagittal vertical axis offset of less than a predetermined value.

Yet other implementations of the above described methods involve the determining the dynamic range of motion of the vertebrae being performed by determining the extent of rotation of a vertebra under the bending, around at least one of its axial, lateral and AP axes. Alternatively, the determining the dynamic range of motion of the vertebrae may be performed by registration of an image of a vertebra from the two dimensional images in positions of bending or standing of the subject, with a matched image of the corresponding vertebra from the three dimensional images.

In any of the above described methods, the alignment optimization of the vertebrae of the spine may comprise the virtual adjustment of the three-dimensional images of the subject's spine according to predetermined values of the spino-pelvic parameters and compensatory mechanisms of the subject's spine.

Additionally, the images of the subject's spine in positions of bending of the subject may be obtained either from two dimensional X-ray images of the subject, or from two dimensional images derived from three dimensional image sets of the subject. Three-dimensional images of the subject's spine in its erect neutral position may be obtained by a predetermined conversion of three-dimensional image data of the subject's spine in a supine or prone position.

Any of the above described methods may further comprise the step of generating the shape of at least one fusion rod to maintain the vertebrae of the spine in an optimized alignment pose. Such methods may also comprise the step of defining vertebrae where a surgical correction of the spinal anatomy is advised to achieve the alignment optimization. In that case, the surgical correction may comprise posterior column or anterior column correction.

Finally in the above mentioned methods, the vertebrae in a region of interest of the spine may be individual vertebrae, or they may be spinal segments comprising a number of adjoining vertebrae.

Still other exemplary implementations involve a method of planning the correction of spinal deformations of a subject, comprising:
(i) obtaining three-dimensional images of the subject's spine in its erect neutral position,
(ii) obtaining additional two-dimensional images of the subject's spine in positions of full bending achieved by the subject,
(iii) obtaining at least one parameter quantizing the limit of at least one of translational and orientational motion of vertebrae of the patient's spine in the positions of full bending, and
(iv) adjusting the virtual positions of the vertebrae in the three-dimensional images according to a procedure for reducing spinal deformations apparent in the three-dimensional images of the subject's spine,
wherein the step of adjusting the virtual positions of the vertebrae is performed taking into account limitations arising from the at least one parameter quantizing the limit of at least one of translational and orientational motion of vertebrae of the patient's spine.

In such a method, the positions of full bending may comprise at least one of bending to the right, bending to the left, bending in flexion, bending in extension, and rotation. Furthermore, the procedure which reduces spinal deformations apparent in the three-dimensional images of the subject's spine may comprise an optimization to generate a straightened spinal alignment in the coronal plane. Alternatively, it may comprise an optimization of the spinal alignment in the sagittal plane. In the latter case, the optimization of the spinal alignment in the sagittal plane may involve manipulation of sagittal parameters according to a procedure which generates a sagittal vertical axis offset of less than a predetermined value.

In any of these latter mentioned methods, the at least one parameter may be the extent of at least one of axial, AP or lateral rotation of a vertebra. Additionally, the three-dimensional images of the subject's spine in its erect neutral position may be obtained by a predetermined conversion of three-dimensional image data of the subject's spine in a supine or prone position.

BRIEF DESCRIPTION OF THE DRAWINGS

The present invention will be understood and appreciated more fully from the following detailed description, taken in conjunction with the drawings in which.

DETAILED DESCRIPTION

Figure 2:
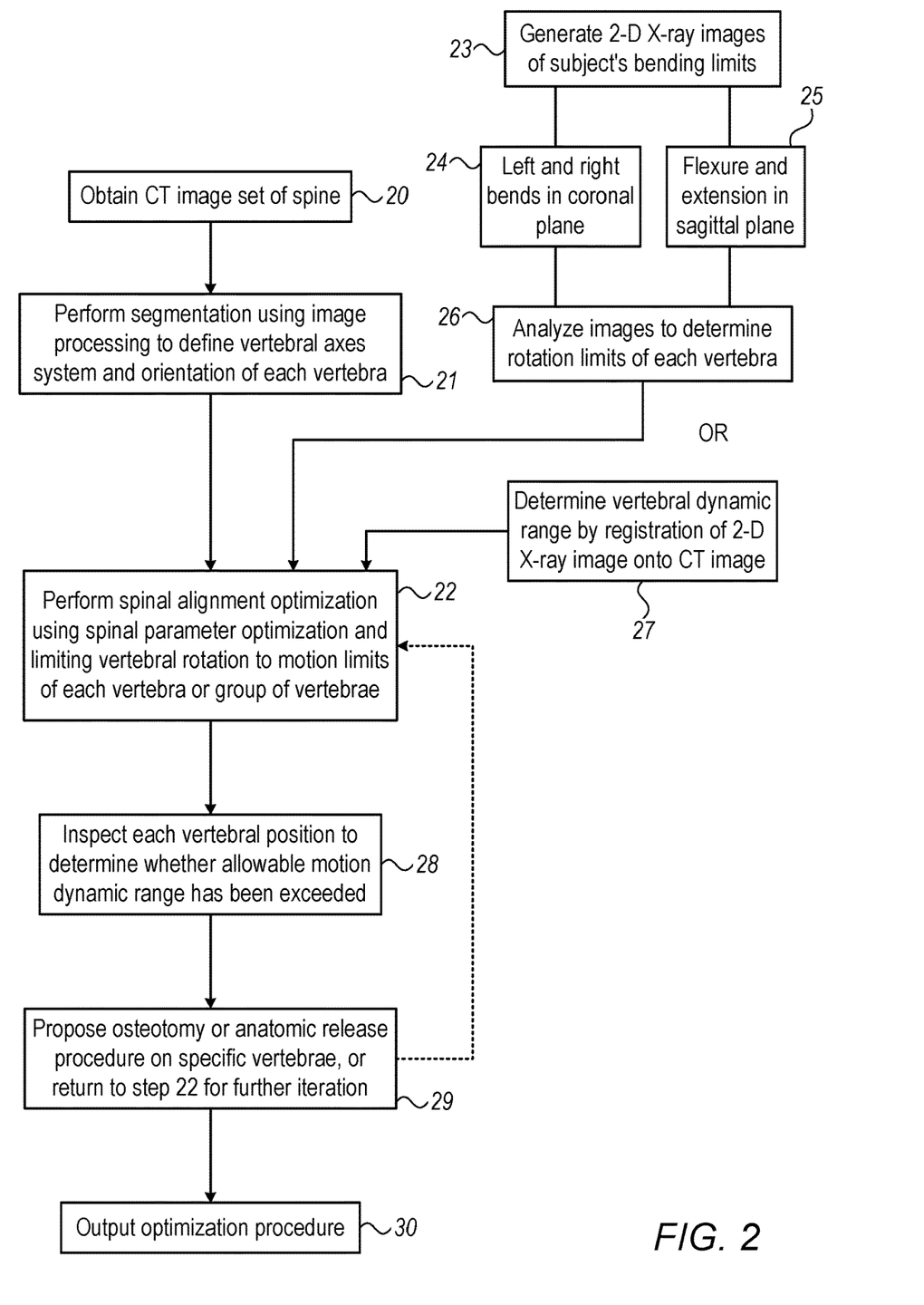
FIG. 2 shows a flow chart illustrating schematically a method of analyzing the subject's spinal curvatures in order to predict and provide instructions for a process to provide an optimum corrected alignment of the spine.

Reference is now made to FIG. 2, which shows a typical flow chart illustrating schematically an exemplary method according to the present disclosure, of analyzing the subject's spinal curvatures, in order to predict and provide recommendations for a process to provide an optimally improved alignment of the spine. The details of every step of the methodology used in the flow chart of FIG. 2 are not meant to be exclusively specific, and only certain aspects relate to the advantages of the presently disclosed methods. Details of steps requiring further explanation are illustrated in the drawings following that of FIG. 2. Throughout the Detailed Description section of this disclosure, the Schwab parameters are used to define sagittal spinal positions and angles, as very widely used in the field, and the Cobb angles and other related parameters are used to define coronal spinal positions and angles.

In step 20, a three dimensional image set of the subject's spine is obtained, such that the spinal structure can be examined in three dimensions, and over the whole of its length if so required by the correction of the spinal section(s) envisaged. The image set should be of the subject's spine in an erect position, known as the neutral position or the natural anatomic posture. The image set may either be obtained directly by an imaging system which can obtain three-dimensional images of the subject while standing, or alternatively, if the three-dimensional image set can only be obtained while the subject is lying down, such as for most CT imaging systems, then the prone or supine image sets have to be converted to a representation of the erect images, taking into account the changes which occur in the position of the vertebrae as the spine becomes upright and hence weight bearing.

In step 21, segmentation is performed on the region of the spine of interest, which will often be the whole length of the spine though the present method may also be applied to limited segments of the spine. The position and orientation of each vertebra may be defined by use of feature extraction, though any other form of image processing which can provide that data is equally acceptable, such as image processing routines that are configured to recognize pedicles, endplates and the spinal canal. This may be conveniently performed by marking planes parallel to the end plates of the vertebral bodies, such as detected by the feature extraction techniques of the image processing procedure used. Segmentation of an exemplary scoliotic deformed spine is shown in the coronal views depicted in FIGS. 3A to 3D hereinbelow. In the coronal plane, the object of the procedure is to obtain the best possible alignment of all of the planes parallel to each other over the length of the spine, which is the equivalent of the straightening of the spine according to the natural biomechanical movement.

In step 22, the spinal alignment parameters, such as the sagittal parameters PI, PT, SS, LL, TK and SVA, and the coronal parameters, such as the Cobb angles, and parameters such as the well-known AVT-T, AVT-L, CD and RAD parameters, are calculated from the segmentation measurements, and a spinal alignment optimization is performed in both coronal and sagittal planes in order to achieve an optimally balanced spine having acceptable global balance parameters. One exemplary sagittal optimization procedure is outlined in FIG. 5 below, in which a predetermined maximum value of SVA is used as the definitive parameter for determining whether the optimization has achieved its aim, though other schemes for the outline sagittal optimization can also be used. The optimization is performed by applying predetermined limitations for the classical spinal alignment parameters, such as those mentioned above. However this alignment optimization differs significantly from prior art procedures, in that according to the present methods, account is taken of the dynamic range of each of the subject's vertebrae in order to achieve the optimum global alignment by reorientation or repositioning of the individual vertebrae. The anatomical constraints of each vertebra relative to its immediate neighbours, such as the distance between two vertebrae, the rotation axes of each vertebra, and other geometrical limitations, are also taken into account in this optimization step. Additionally, distribution of the realignment may also take into account any biomechanical rules for expected flexibility of different sections of the spine, such as the suggested criterion mentioned below that the total realignment should be divided such that one third falls between L1 and L4, and two thirds between L4 and S1.

The above-mentioned dynamic ranges of mobility of each of the vertebrae are most simply obtained by first generating, in step 23, a number of two-dimensional X-ray images of the subject bending to his/her maximum comfortable abilities in a number of predetermined directions. Although two-dimensional X-ray images of the simplest method of obtaining the images of the range of motion (ROM) of the subject, it is to be understood that any other method of obtaining such two-dimensional information can also be used, such as derivation from three-dimensional image sets of the person bending and flexing. Typically bending to left and right, as shown in step 24, is used in order to determine the extent of flexibility or motion of the vertebrae in the coronal view, using AP images, while maximum flexion and extension of the subject's spine is obtained in the sagittal view, using lateral images, as shown in step 25. Additional information may be obtained by generating 2-D X-ray images of the subject twisting his/her spine to the maximum comfortable extent. Including the erect X-ray image, a total of up to six 2-dimensional X-ray images may be used to define the dynamic limits of mobility of each of the subject's vertebra. In cases in which, instead of each individual vertebra, complete spinal segments are used for performing the methods of this disclosure, the data obtained will be for those spinal segments. In the description which follows, the case of the alignment analysis of individual vertebrae will be followed.

The dynamic range of each vertebra can be calculated by one of two methods:

(i) In step 26, the axial rotation of each vertebra is determined by analysis of the 2-D images, such as by the methods to be shown in FIG. 3 below, and using the techniques for automatic axial rotation measurement based on 2-D X-ray images, as described in the article titled "The Radiographic Method for Evaluation Of Axial Vertebral Rotation—Presentation of the New Method" by P. Cerney et al., published in Scoliosis Vol. 9:11 pages 1748-7161 (2014). For each vertebra, as an example, the limits of the motion can be tabulated in the form of the maximum bending angles for flexion and extension, and the limits of bending to the right and the left, and the AP and LT angles.

(ii) Alternatively in step 27, the dynamic range is calculated by performing a registration or spatial correlation between the shape of each vertebra in the 2-D X-ray images, and the corresponding vertebrae in the CT images as determined by the closest matching resulting from projecting of the vertebral shape from the X-ray image onto a selected viewing plane of the CT images. By this means, the bending limitation of any vertebra obtained from a 2-D X-ray image, can be impressed on a fully 3-dimensional representation of the vertebra. Thus, by registering the 2 dimensional X-ray images to the CT image set, a three-dimensional model of each vertebra can be generated, including the three-dimensional range of motion which the subject can achieve.

Either of these methods of determining the dynamic range of the vertebrae is then used as inputs in step 22, in determining the optimally aligned spine curvature, taking into account any limitations imposed by the dynamic range of specific vertebrae. These dynamic range-of-motion limitations can be applied either at the micro-level or at a more macro-level. In the former case, in the optimization process, every vertebra can have changes to its orientation and position as restrained by the allowable rotation, limited by the data obtained in the preplanning 2-D X-ray bending images. At a more macro level, the division of realignment of the vertebra may also be governed by predetermined decisions as to overall realignment of sections of the spine, such that if it transpires that a certain vertebra is more severely limited than, for instance, its immediate neighbors, the method can decide to redistribute the total required realignment over a number of vertebrae, such that the more limited motion vertebra is realigned or reoriented less than optimally, and the missing correction level is spread out over neighboring vertebrae, thus achieving the required realignment optimization, yet without the need for surgical intervention on the vertebra with the problematic motion range.

Furthermore, the division of realignment of the vertebra may also be governed by predetermined anatomical decisions, based on the known biomechanical properties of groups of vertebrae. Thus, for example, if a certain level of realignment is indicated over a certain segment of the spine by the optimization procedure, and it is known anatomically that certain vertebrae in that section are more mobile than others, the division of the realignment can be performed taking that anatomical knowledge into account. For example, for a specifically indicated realignment of the lower section of the spine, it may be advisable to divide the total realignment such that one third falls between L1 and L4, and two thirds between L4 and S1, or other defined divisions. In general the manipulation on the CT scan imitates the natural movement of each vertebra separately and relative to the other vertebrae. Thus, the rotation is angular, around the joint, and the distance between every adjacent pair of vertebrae is constant.

The result of these steps enables the generation of a 3 dimensional image set for presenting to the surgeon, in which the range of motion of each vertebrae is indicated, such that the surgeon can decide for each vertebra, whether correction of the global spinal alignment can be performed at that vertebra or not. A method of improvement of global motion is therefore performed by considering each vertebrae and deciding at which points to attempt to improve the subject's overall motion. In other words in vertebra or regions where the range of motion is limited, or even nonexistent, the surgeon may decide to ignore that vertebra or region, regarding it as being completely immobile, when planning the complete spinal alignment, or the surgeon can decide to provide motion at that level by means of surgical correction, such as osteometric resection or posterior release. In regions where a full range of motion is available, the surgeon knows that that full range may be used in planning the complete spinal alignment, and that no surgical intervention is required at that spinal level. The "full range of motion" may be determined either by using a database of the biomechanical motion parameters of each vertebra of the spine in a spinally healthy population, or by using the subject's own overall total motion, and defining the range of motion of individual vertebrae or segments of the spine of the subject, in comparison with the subject's total motion range. Conversely, if the surgeon wishes to generate a spinal alignment plan which would involve relative motion of a specific vertebral pair beyond the capabilities of the range of motion of that vertebral pair, a warning will be given to the surgeon either that that alignment plan is invalid, or if it is to be used, that surgical correction will be needed at that specific vertebral pair. In further implementations of the methods of this disclosure, the decisions regarding which vertebra need surgical correction, which need motion limitation such as by the application of fusion rods, and which can utilize their natural flexibility, in planning the global spinal alignment, can be automated using the computer control to perform the iterative adjustments needed to achieve the optimum result within the limitations of the range of motions of each vertebral level.

The outcome of this procedure is a complete spinal alignment plan, having a value for the SVA parameter in the sagittal plane, or of another parameter similarly used such as the CD and RAD in the coronal plane, within the limits employed to define a spine alignment providing adequate global balancing of the subject. Each vertebra of this optimized alignment can then be inspected in step 28 to check whether the vertebral orientation and positioning proposed by the optimization procedure is possible within the dynamic range of the subject, as determined in steps 23 to 27. If any of the vertebrae show that the reorientation or motion required to achieve the predicted position, as generally determined by the required rotation of the vertebra, is indeed beyond the abilities of its dynamic range, then two possibilities exist. The method can suggest either an osteotomy procedure on that particular vertebra, or an anatomical release procedure, as shown in step 29. Common surgical correction techniques used in this step include pedicle subtraction osteotomy (PSO), Smith-Peterson osteotomy (PSO) and vertebral column resection (VCR) techniques.

Figure 5:
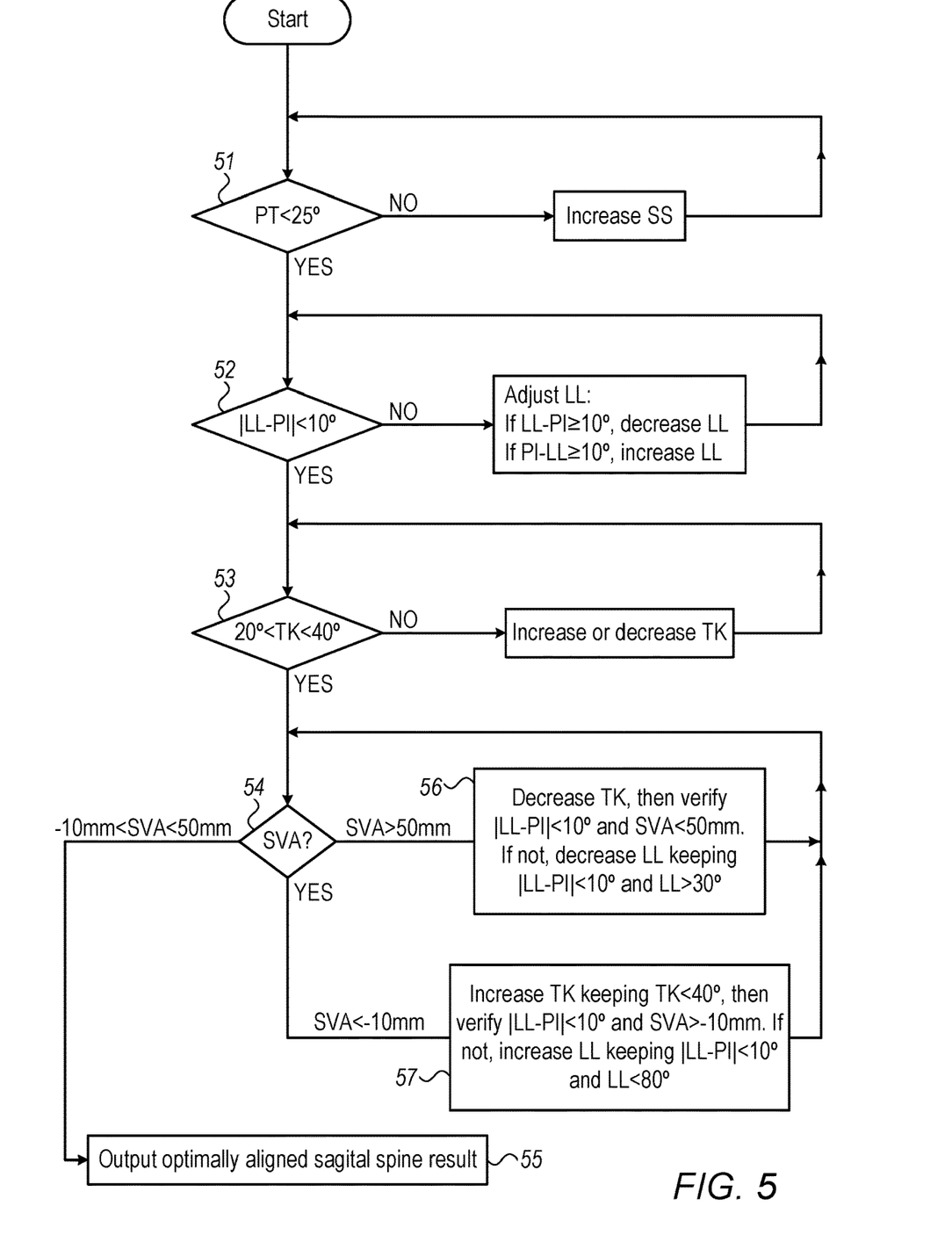
FIG. 5 illustrates a flow chart for an exemplary iterative sagittal alignment optimization procedure, executed in order to achieve an optimally balanced spine having acceptable global balance parameters.

An alternative process can be envisaged in which the dynamic range limitations of each vertebrae as determined by the 2-D X-ray images, are not taken into account initially during the optimization procedure shown in FIG. 5 below, but rather that the optimization is performed without any consideration of the individual vertebral dynamic range limitations, until the optimal spinal parameter(s) is achieved. FIG. 5 below uses a sagittal optimization procedure for optimizing the SVA measurement, but it is to be understood that this is only one example of the way in which the global alignment can be optimized, and alternative procedures could also use other spinal parameters such as PT, PI-LL, TK or LL in the sagittal plane, or the Cobb angles, CD or RAD in the coronal plane optimization. At this point the decision as to how to proceed can be taken by the automatic procedure, which can review the orientation and position of each vertebra as determined by the optimal global alignment solution, and can determine whether these new orientations and positions are within the dynamic range possible for each vertebra. Should the obtained solution suggest that any vertebra be moved beyond its clinical mobility limits, the method can propose either proposeanatomic release of the problematic vertebrae, or osteotomy of neighboring vertebrae to constrain motion of the problematic vertebrae to their determined limits. As an alternative, the physician may review each of the proposed vertebral reorientations of the ideally corrected alignment, including the mobility limitations, and can make his/her proposals as to how to amend the generated alignment, according to his/her preferred operative techniques, which can be simulated using the program software. The final step of the process in step 30 is then the output of the complete optimization plan, which can include surgical proposals, and/or screw positions and fusion rod shapes.

Figure 3A:
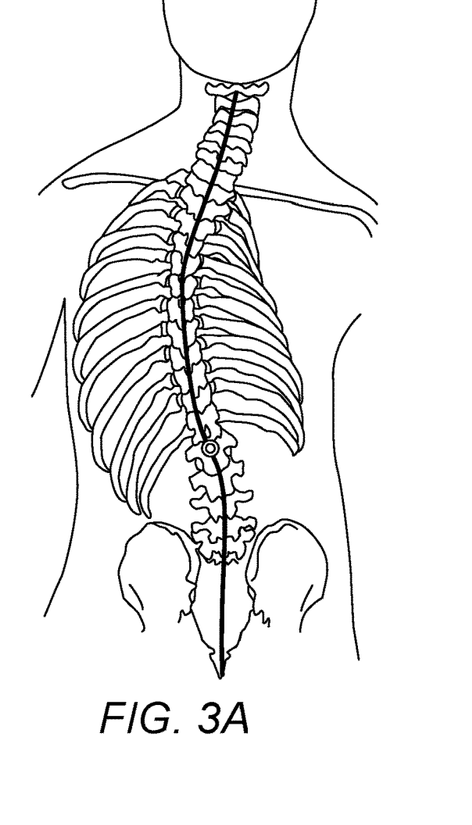
FIGS. 3A to 3E illustrate schematically how the automatic segmentation and labelling of the separate images of the vertebrae of the spine, and their angular alignment can be performed.
Figure 3B:
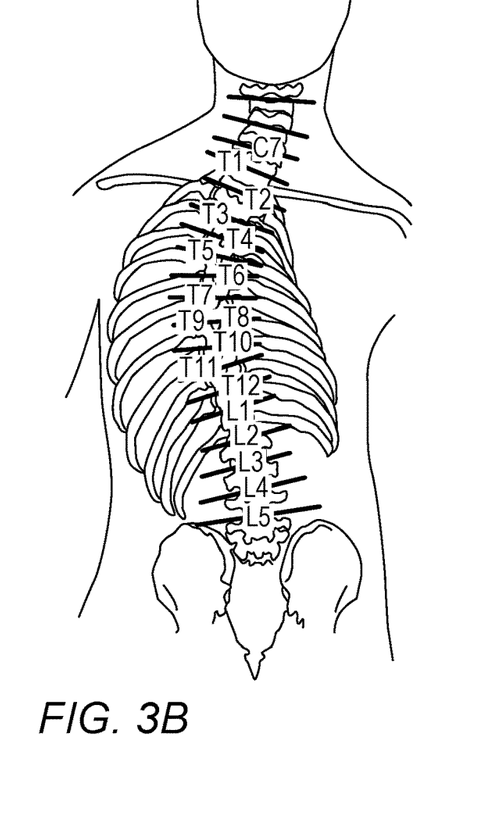
Figure 3C:
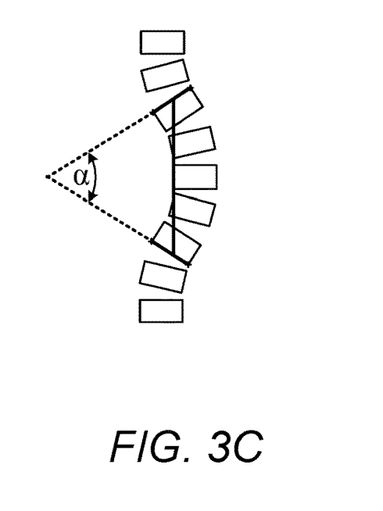
Figure 3D:
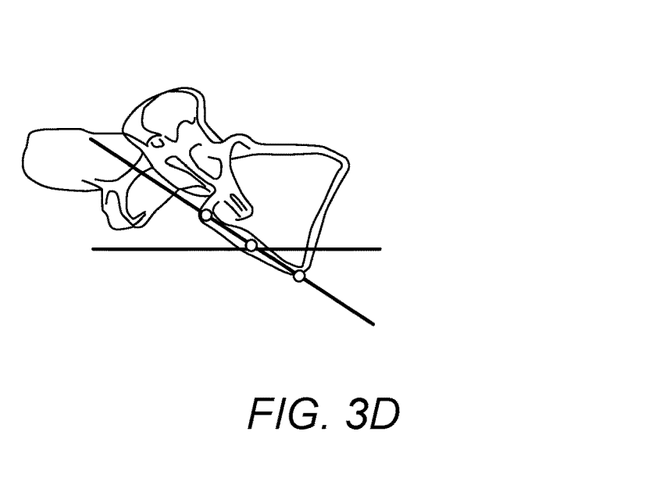
Figure 3E:
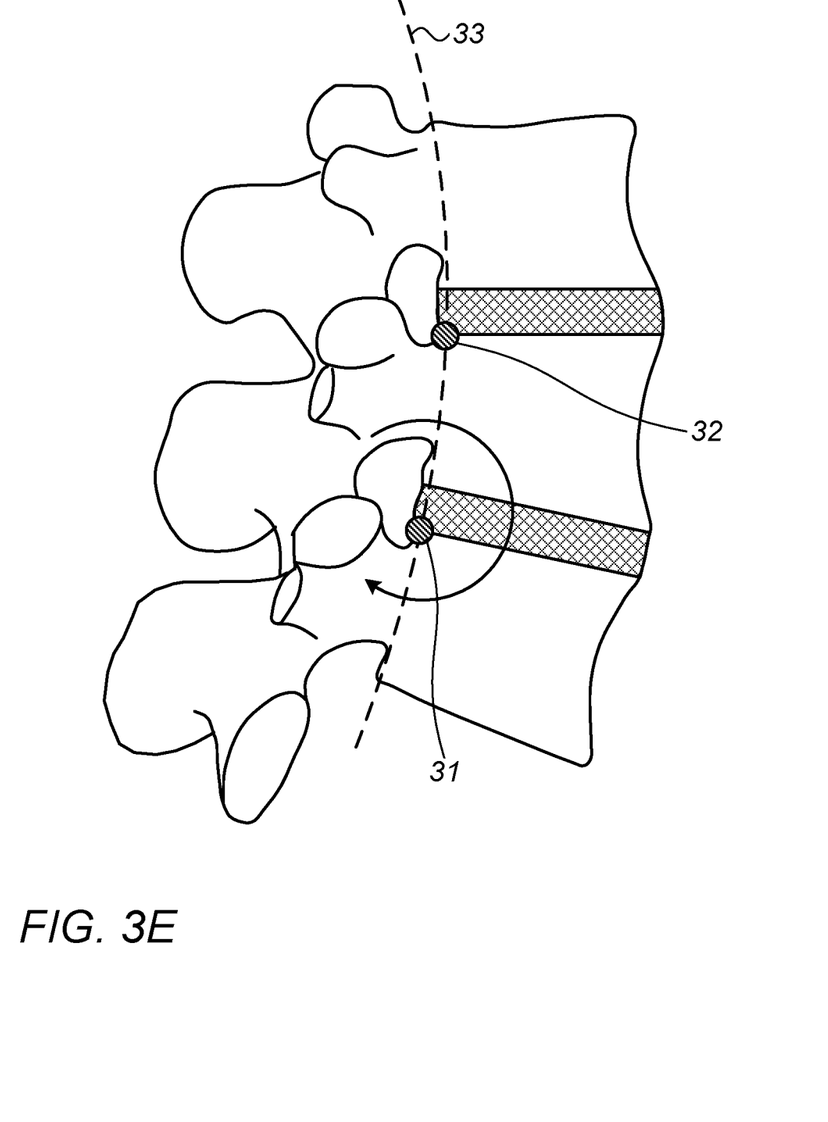

Reference is now made to FIGS. 3A to 3E, which illustrate how the automatic segmentation and labelling of the separate vertebrae of the spine is performed. In FIGS. 3A to 3C, an example of the segmentation in the coronal view of the spine is shown on an AP X-ray image. The scoliotic nature of the curvature of the subject's spine is shown in FIG. 3A, with the midline of the spine shown in FIG. 3A being marked by the software using image processing techniques. In the example program shown, the particular vertebra from which measurements can be extracted is shown by the dot and the vertebral identification is displayed on screen by the bold line. In FIG. 3B, there is shown an example output of the segmentation process, showing the slope of each of the endplates of the vertebrae, and the vertebral labelling in the coronal view direction. In FIG. 3C, a computer representation of the angles of each endplate of a selected segment of the spine is shown, showing how a sectional included angle can be defined between selected vertebrae, as shown by the angle $\alpha$ between the bold lines on the two marked vertebra. In FIG. 3D there is shown a method by which the program determines the vertebral endplate inclination, using a line impressed on the endplate by means of feature extraction techniques. The content of FIGS. 3A to 3D are only examples of how the disclosed segmentation method can be implemented, and are not intended to limit the method in any way. Finally, FIG. 3E shows the manner in which the image tilt motions used in the optimization process are performed about the Instantaneous Axis of Rotation (IAR) 31, 32, where the neutral axis 33 is marked running through the IARs. While tilting the image, the biomechanical movement of the spine is imitated by rotating each vertebra around the instantaneous point of rotation and thus keeping the distance between adjacent points of rotations constant. The advantage of this feature will be explained hereinbelow.

Figure 4A:
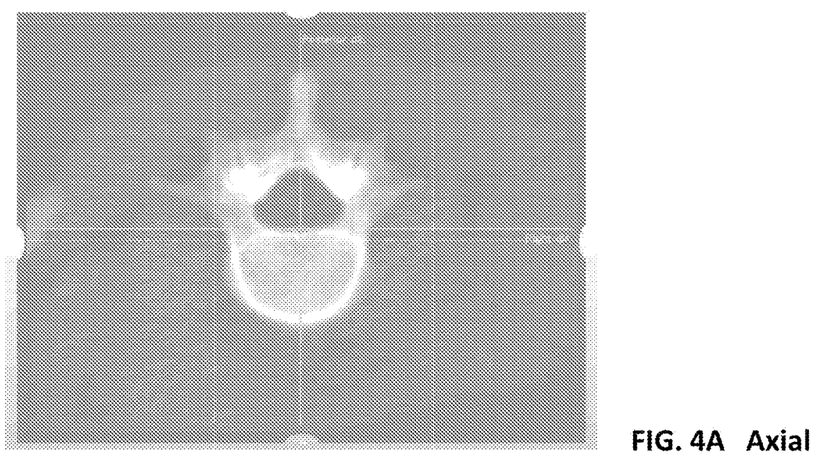
FIGS. 4A to 4C illustrate one method by which the rotational axis of a vertebra can be defined for the axial, lateral and AP directions respectively.
Figure 4B:
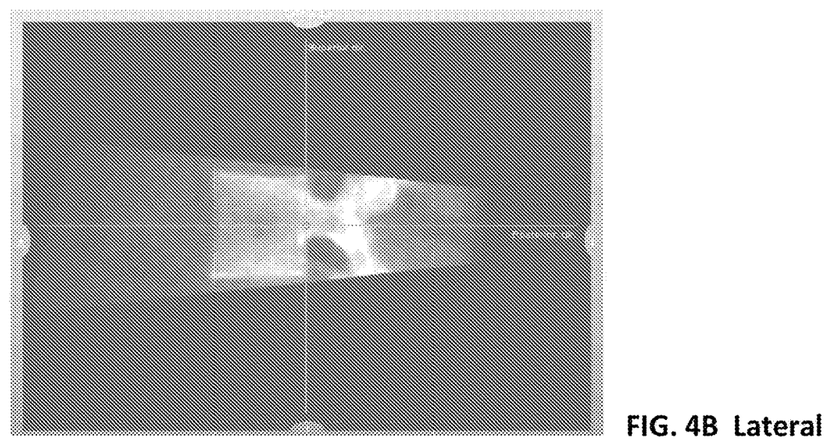
Figure 4C:
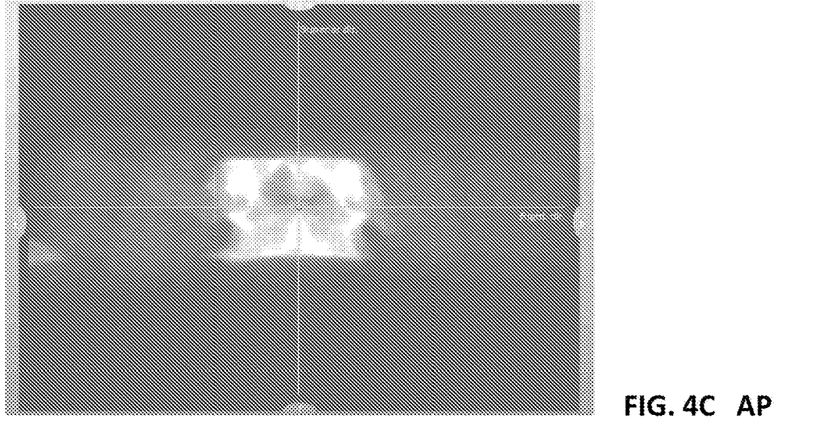

Now that the individual vertebrae have been identified, it is necessary to define their orientation and position, in order to be able to characterize the entire vertebral structure of the spine, as imaged in the CT data set. Only when such a characterization has been achieved is it possible to attempt to optimize the alignment of the spine, whether in the coronal direction where a straight line alignment is generally sought after, or whether in the sagittal direction, where a number of sagittal alignment parameters optimized, as will be shown hereinbelow in the exemplary algorithm of FIG. 5. In order to characterize the position and orientation of each vertebra, the axis of each vertebra must first be defined in the CT images. A reference method of defining the axial, lateral and AP axes should be used. Reference is now made to FIGS. 4A to 4C, which show CT images of a vertebra in axial, lateral and AP views, in order to illustrate how an exemplary system of defining the vertebral orientation and axes can be achieved.

In FIG. 4A, an axial CT image of a vertebra is shown with the axial axis defined at the posterior edge of the vertebral body and perpendicular to the end plate, relative to the vertical (spinous process direction) and horizontal (transversal process direction) crosshair lines. This axis is used to define the axial rotation of the vertebra, and every individual vertebra has its own defined axial axis. The relation between successive axial axes defines the relation between the orientation of adjacent vertebrae, and this information is necessary in order to attempt to line up one vertebrae of the other in optimizing the spinal alignment.

In FIG. 4B, a lateral CT image of the same vertebra is shown, with an axis of rotation defined as lying on the lower part in the pedicle, at the you intersection of the posterior longitudinal ligament (PLL) and the pedical inferior wall, and may be conveniently defined as lying on the inferior and posterior point of the pedicle column.

In FIG. 4C, an AP CT image of the vertebra is shown and the axis of rotation is defined as being at the center of the centerline between the bottom edges of the two pedicles.

Once these axes have been defined for each vertebra, it is possible to define the position and orientation of each vertebra, and hence any translation and rotation motions of a vertebra generated in accordance with an optimization program can be performed on vertebrae having known positions and orientations in three dimensions. As formalized in the article entitled "Biomechanics of Spinal Deformities" by R. P. Schlenk et al, published in Neurosurg.

Focus, Vol. 14(1), 2003, the six fundamental segmental movements or types of deformation of the spine along or around the Instantaneous Axis of Rotation (IAR) are: (1) rotation or translation around the long axis (A); 2) rotation or translation around the coronal axis (B); 3) rotation or translation around the sagittal axis (C); 4) translation along the long axis (A); 5) translation along the coronal axis (B); and 6) translation along the sagittal axis of the spine (C).

Once the axis of each vertebra has been obtained, the segmentation data is used in order to derive parameters that relate to the alignment and position of the vertebrae in the region of interest, relative to the entire spinal alignment plan.

Typically, the spinal parameters are obtained such as the parameters LL, TK, PI, PT, SVA for the sagittal alignment direction, based on the geometry (mainly angles) of the vertebral alignments.

Starting from the inferior segment (Pelvic Tilt measurement) and up to the SVA (Cervical measurement) each parametric value is obtained by geometrically measuring the angles between the two lines that create the measurement, as described in FIG. 3C above.

If the value is not within the "normal range" that is predefined according to atlases based on big data obtained from a large population of healthy subject, relative to patient age, gender and ethnicity, the parameter is increased or decreased by tilting the image around the pivot point, manipulating the CT scan by moving each pixel to create the desired movement. All image tilt motions are performed about the Instantaneous Axis of Rotation (IAR) 31, 32, as shown in FIG. 3E, where the neutral axis 33 is marked running through the IARs. While tilting the image, the biomechanical movement of the spine is imitated by rotating each vertebra around the instantaneous point of rotation and thus keeping the distance between each two point of rotations constant, such that there is no effective change of length of the spine, which is an important requirement. Rotation of vertebrae around any axis of rotation results in linear motion of the vertebrae; relative to each other. When flexing, the axis of rotation moves anteriorly, when extending, the axis of rotation moves posteriorly, hence the use of the term instantaneous axis of rotation, since the center of rotation moves with spinal movement. By using the instantaneous axis of rotation, the effect of this motion of the vertebrae, closer or further apart, is nullified. In FIG. 3E, the neutral axis running through the IAR's is located close to the center of the spinal cord, such that by performing rotations about those IARs, no extension of the spinal cord is engendered, and the integrity of the spinal cord is thus maintained.

Rotation of vertebra by vertebra continues using an iterative algorithm, to be described in FIG. 5, until all of the desired spinal parameters are within the normal range.

Reference is now made to FIG. 5, which illustrates a flow chart for an exemplary iterative sagittal alignment optimization procedure, intended in this example, to bring the value of the SVA parameter to within a predetermined maximum value. As previously stated, an SVA within a certain maximum value is an indication that good global balance will be achieved for the subject with such an optimized spinal alignment. Typically, a maximum SVA value of 50 mm. is used in the present example, and a negative value of SVA is limited to −10 mm, though these levels are dependent upon the physician's preferences, which could also be influenced by the subject's individual abilities. Other criteria for SVA, or even another parameter, could also be used in this sagittal optimization. The decision to use SVA as the criterion for determining optimized spinal alignment complies with the use of the "spino-pelvic parameters" as some of the main parameters used in the algorithm to optimize the spinal alignment, these having a direct effect on the spinal balance of a standing subject, as clearly shown in some of the above cited references. Some of the measurements and parameters used, such as PI and PT, which are related to the hip axis, which is the joint that follows the knee joint, support this position. The algorithm illustrated in the flow chart of FIG. 5 is based on known compensatory mechanisms between the spinal segments. Thus for instance, changing the Thoracic Kyphosis (TK) has a direct effect on the Lumbar Lordosis (LL), and changing the SVA directly affects the TK angle.

In the example flow algorithm shown in FIG. 5, the following criteria are selected for the limits of the various sagittal spinal parameters, though as previously stated, the specific limits used may vary from physician to physician according to personal professional preferences, and according to the patient's characteristics, such as age, gender and ethnicity:

PI=PT+SS
PT<25°
|LL−PI|<10°
30<LL<80°
20<TK<40°
−10°<SVA<50 mm,
0°<Cobb<10°

In step 51, the value of PT is determined, and if found to be greater than 25°, the sacral slope SS is increased by a predetermined angle, typically 1°, though if the value of PT is significantly greater than 25°, a larger initial incremental angle could be used. The PT is again measured, and this iteration is repeated until the value of PT becomes less than 25°.

Once the value of PT is less than 25°, in step 52, the absolute value of LL−PI is measured and if not less than 10°, the value of LL is increased or decreased in order to attempt to bring the absolute value of LL−PI to less than 10°. In other words, this step of the optimization is intended to ensure that the difference between the LL angle and the PI angle is kept to less than 10°, regardless as to whether LL or PI is the bigger angle. In order to ensure this, the value of LL is increased or decreased depending on whether the actual value of LL−PI is positive or negative. If LL is the dominant angle, and LL is more than 10° larger than PI, then LL is decreased incrementally. Conversely, if PI is the dominant angle, and PI is more than 10° larger than LL, then LL must be increased incrementally.

Once the absolute value of LL−PI is less than 10°, in step 53, TK is measured, and it is determined whether TK falls between 20° and 40°. If not, the value of TK is increased or decreased in order to bring TK within the desired range.

Once TK falls within the desired range, in step 54 the value of SVA is measured. If the value of SVA is greater than 50 mm. or smaller than −10 mm., the angle TK is increased or decreased in order to bring SVA to within the range of −10 mm. to 50 mm., i.e. that the C7 plumb line falls anterior to the posterior-superior corner of the S1 endplate. If SVA is greater than 50 mm., TK is decreased. If SVA is still greater than 50 mm, then LL is increased up to 80°, while still ensuring that |LL−PI| is less than 10°. If SVA is found to be less than −10 mm., TK is increased in order to attempt to bring SVA to within the normal range. If SVA still cannot be brought positive, then LL is decreased down to a level of 30°, while still ensuring that |LL−PI| is less than 10°. Since the value of LL will have changed with change in TK, after any of these steps, the value of |LL−PI| is again measured to ensure that that criterion is still upheld.

Once the value of SVA has been brought to be within the range of −10 mm. to 50 mm, the sagittal alignment procedure is considered to have been optimized at step 55, and the position and orientation of each of the vertebrae constitutes the optimized spine, which the physician implements in the main optimization algorithm shown in FIG. 2.

It is appreciated by persons skilled in the art that the present invention is not limited by what has been particularly shown and described hereinabove. Rather the scope of the present invention includes both combinations and subcombinations of various features described hereinabove as well as variations and modifications thereto which would occur to a person of skill in the art upon reading the above description and which are not in the prior art.

The invention claimed is:

1. A method of planning the correction of spinal deformations of a subject, comprising:
performing segmentation of at least one three-dimensional image of the subject's spine in its erect neutral position, such that positions and orientations of at least some vertebrae in a region of interest of the spine are characterized;
calculating spinal parameters from the segmentation that relate to an alignment and position of at least one vertebra in the region of interest;
determining a dynamic range of motion of the at least one vertebra by analyzing at least one two- or three-dimensional image of the subject's spine in a position of bending of the subject; and
when the spinal parameters do not fall within a predetermined acceptable range desired to optimize a global balance of the subject, identifying alignment changes of the at least one vertebra in the region of interest of the spine which would result in bringing the spinal parameters within the acceptable range, to reduce the spinal deformations of the subject's spine,
wherein the identified alignment changes of the at least one vertebra are such that an allowable motion of the at least one vertebra will not extend beyond the dynamic range of motion of the at least one vertebra.

2. The method of claim 1, wherein the identified alignment changes are based on at least in part on biomechanical considerations over the entire length of the subject's spine.

3. The method of claim 1, wherein the spinal parameters relate to at least some mutual angles, projections and linear positions generated by the vertebrae in the region of interest.

4. The method of claim 1, wherein the determining as to whether the spinal parameters fall within the predetermined acceptable range is performed either automatically by image processing, or by manual measurement on images, or based on medical personnel judgment or experience.

5. The method of claim 1, wherein the positions of bending of the subject comprise at least one of bending in a first lateral direction, bending in a second lateral direction opposite the first lateral direction, bending in flexion, bending in extension, and rotation.

6. The method of claim 1, wherein the identified alignment changes comprise at least one of an optimization to generate a straightened spinal alignment in a coronal plane and an optimization of the spinal alignment in a sagittal plane.

7. The method of claim 1, wherein the identified alignment changes involve manipulation of sagittal parameters according to a procedure which generates a sagittal vertical axis offset of less than a predetermined value.

8. The method of claim 1, wherein the determining the dynamic range of motion of the at least one vertebra is performed by determining an extent of rotation of the at least one vertebra under bending around at least one of its axial, lateral and AP axes.

9. The method of claim 1, wherein the at least one two- or three-dimensional image of the subject's spine in positions of bending is obtained from at least one of (i) a two-dimensional X-ray image of the subject or (ii) a two-dimensional image derived from a three-dimensional image set of the subject, in which the dynamic range of motion of the at least one vertebra is determined by matching corresponding vertebrae from the two dimensional image with those from the three-dimensional image set.

10. The method of claim 1, wherein the identified alignment changes comprise a virtual adjustment of the at least one three-dimensional image of the subject's spine according to predetermined values of at least one of (i) spino-pelvic parameters and (ii) a level of compensatory mechanisms of the subject's spine.

11. The method of claim 1, wherein the at least one three-dimensional image of the subject's spine in its erect neutral position is derived by conversion of three-dimensional image data of the subject's spine in a supine or prone position.

12. The method of claim 1, further comprising the step of calculating a shape of at least one fusion rod to maintain at least the vertebrae in the region of interest of the spine in an optimized alignment pose.

13. The method of claim 1, further comprising the step of defining a surgical correction of at least one vertebra to achieve the identified alignment change.

14. The method of claim 1, wherein the vertebrae in the region of interest of the spine are spinal segments comprising a number of adjoining vertebrae.

15. The method of claim 1, wherein when the identified alignment changes are such that the motion achieved of the at least one vertebra exceeds the dynamic range of motion of the at least one vertebra, surgical intervention on at least the at least one vertebra is indicated.

16. A method of planning the correction of spinal deformations of a subject, comprising:
obtaining three-dimensional images of the subject's spine in its erect neutral position;
obtaining additional two-dimensional images of the subject's spine in positions of full bending achieved by the subject;
obtaining at least one parameter quantizing a limit of at least one of translational and orientational motion of at least one vertebra of the subject's spine in the positions of full bending; and
determining an adjustment of a virtual orientation and position of the at least one vertebra in the three-dimensional images according to a procedure for reducing spinal deformations that are apparent in the three-dimensional images of the subject's spine,
wherein the determined adjustment does not require a translational or orientational motion of the at least one vertebra that would exceed the at least one parameter.

17. The method of claim 16, wherein the positions of full bending comprise at least one of bending in a first lateral direction, bending in a second lateral direction opposite the first later direction, bending in flexion, bending in extension, and rotation.

18. The method of claim 16, wherein the procedure which reduces spinal deformations that are apparent in the three-dimensional images of the subject's spine comprises at least one of (i) an optimization to generate a straightened spinal alignment in a coronal plane, (ii) an optimization of the spinal alignment in a sagittal plane, and (iii) manipulation of sagittal parameters according to a procedure which generates a sagittal vertical axis offset of less than a predetermined value.

19. The method of claim 16, wherein the at least one parameter is the extent of at least one of axial, AP, or lateral rotation of a vertebra.

20. The method of claim 16, wherein the three-dimensional images of the subject's spine in its erect neutral position are derived by a conversion of three-dimensional image data of the subject's spine in a supine or prone position, taking into account any changes which would occur in an orientation and position of the at least one vertebra, as the spine of the subject would become upright and hence weight bearing.

21. A method of planning the correction of spinal deformations of a subject, comprising:

performing segmentation of at least one three-dimensional image of the subject's spine in its erect neutral position, such that positions and orientations of at least some vertebrae in a region of interest of the spine are characterized;

calculating spinal parameters from the segmentation that relate to an alignment and position of at least one vertebra in the region of interest;

determining a dynamic range of motion of the at least one vertebra by analyzing at least one two- or three-dimensional image of the subject's spine in a position of bending of the subject; and when the spinal parameters do not fall within a predetermined acceptable range desired to optimize a global balance of the subject, identifying at least one alignment change of the at least one vertebrae which would result in bringing the spinal parameters within the acceptable range, to reduce the spinal deformations of the subject's spine, wherein when the identified at least one alignment change of the at least one vertebra is such that a motion achieved for the at least one vertebra would exceed the dynamic range of motion of the at least one vertebra, a surgical intervention on at least the at least one vertebra is indicated.

* * * * *

UNITED STATES PATENT AND TRADEMARK OFFICE
CERTIFICATE OF CORRECTION

PATENT NO. : 10,777,315 B2
APPLICATION NO. : 15/765720
DATED : September 15, 2020
INVENTOR(S) : Eliyahu Zehavi et al.

Page 1 of 1

It is certified that error appears in the above-identified patent and that said Letters Patent is hereby corrected as shown below:

In the Claims

Claim 2, Column 17, Line 44, delete "changes are based on at least in part on biomechanical" and insert --changes are based at least in part on biomechanical--

Claim 17, Column 18, Line 63, delete the word "later" and insert the word --lateral--

Signed and Sealed this
Ninth Day of March, 2021

Drew Hirshfeld
*Performing the Functions and Duties of the*
*Under Secretary of Commerce for Intellectual Property and*
*Director of the United States Patent and Trademark Office*